United States Patent [19]

Roberts et al.

[11] Patent Number: 5,491,130
[45] Date of Patent: Feb. 13, 1996

[54] PEPTIDE INHIBITORS OF FIBRONECTIN AND RELATED COLLAGEN-BINDING PROTEINS

[75] Inventors: David D. Roberts; Henry C. Krutzsch, both of Bethesda; John M. Sipes, Cabin John; Neng-hua Guo, Gaithersburg; Eric Negre, Bethesda, all of Md.

[73] Assignee: The United States of America as represented by the Department of Health and Human Services, Washington, D.C.

[21] Appl. No.: 973,235

[22] Filed: Nov. 10, 1992

[51] Int. Cl.$^6$ .............................. A61K 38/00; C07K 7/00; C07K 7/06; C07K 7/08
[52] U.S. Cl. ................................ 514/13; 514/15; 514/16; 514/17; 530/328; 530/329; 530/330; 530/327
[58] Field of Search ................................. 514/16–17, 15; 530/330, 329, 328, 325–327

[56] References Cited

U.S. PATENT DOCUMENTS

| | | | |
|---|---|---|---|
| 5,190,918 | 3/1993 | Deutch et al. | 514/15 |
| 5,200,397 | 4/1993 | Deutch et al. | 514/15 |

FOREIGN PATENT DOCUMENTS 0443404  8/1991  European Pat. Off. .

OTHER PUBLICATIONS

Rasheeda S. Zafar et al., "Localization of Two Binding Domains for Thrombospondin within Fibronectin", Archives of Biochemistry and Biophysics, vol. 297, No. 2, pp. 271–276, 1992.
Neng–hua Guo et al, "Heparin–binding Peptides from the Type I Repeats of Thrombospondin" The Journal of Biological Chemistry, vol. 27, No. 27, pp. 19349–19355, Sep. 25, 1992.
Tusynski et al, "Biological Activities of Peptides and Peptide Analogues Derived from Common Sequences Present in Thrombospondin, Properdin, and Malarial Proteins", The Rockefeller University Press, The Journal of Cell Biology, vol. 116, No. 1, pp. 209–217, Jan. 1992.
Jack Lawlor et al, "The Structure of Human Thrombospondin, an Adhesive Glycoprotein with Multiple Calcium–Homologies with Several Different Proteins", The Rockefeller University Press, The Journal of Cell Biology vol. 103, pp. 1635–1648, Nov. 1986.
Joanne E. Murphy–Ullrich et al, "Thrombospondin Modulates Focal Adhesions in Endothelial Cells", The Rockefeller University Press, The Journal of Cell Biology, vol. 109, pp. 1309–1319, Sep. 1989.
Rima Dardik et al, "Multiple Domains are Involved in the Interaction of Endothelial Cell Thrombospondin with Fibronectin", Eur. J. Biochem., Dept. of Polymer Research, Weizmann Inst. of Science, vol. 185, pp. 581–588, Feb. 1989.
Cheryl A. Prater et al, "The Properdin–like Type I Pepeats of Human Thrombospondin Contain a Cell Attachment Site", The Rockefeller University Press, The Journal of Cell Biology, vol. 112, No. 5, pp. 1031–1040, Mar. 1991.
Laszlo Banyai et al, "The Collagen–binding Site of Type–II Units of Bovine Seminal Fluid Protein PDC–109 and Fibronectin", Insti. of Enzymology, Biological Research Center, Eur. J. Biochem., vol. 193, pp. 801–806 Feb. 1990.
Raymond J. Owens et al, "Mapping the Collagen–binding Site of Human Fibronectin by Expression in *Escherichia coli*", The EMBO Journal, vol. 5, No. 11, pp. 2825–2830, 1986.
G. A. Homandberg et al, "Thrombospondin Binds to Amino–Terminal Fragments of Plasma Fibronectin", Thrombosis Research 48, pp. 329–337, 1987, vol. 3, pp. 1635–1648, Nov. 1986.
Frank B. Gelder et al, "Fibronectin Gelatin–binding Activity: Effects of Platelet Thrombospondin, Serum, and Plasma", Louisiana State University, Depts. of Surgery and Medicine, pp. 548–557, Jul 8, 1986.
E. Helene Sage et al, "Extracellular Proteins That Modulate Cell–Matrix Interactions", The Journal of Biological Chemistry, vol. 266, No. 23, pp. 14831–14834, Aug. 15, 1991.
Kenneth M. Yamada, "Adhesive Recognition Sequences", The Journal of Biological Chemistry, vol. 266, No. 20, pp. 12809–12812, Jul. 15, 1991.
Neng–hua Guo et al, "Heparin– and Sulfatide–binding Peptides from the Type I Repeats of human Thrombospondin Promote Melanoma Cell Adhesion", Proc. Natl. Acad. Sci., vol. 89, pp. 3040–3044, Apr. 1992.
Neng–Hua Guo et al, J. Biol Chem, vol. 267, Sep. 25, 1992.

*Primary Examiner*—Jill Warden
*Assistant Examiner*—S. G. Marshall
*Attorney, Agent, or Firm*—Townsend and Townsend and Crew

[57] ABSTRACT

Peptides derived from the second type 1 repeat of human endothelial cell thrombospondin which bind to the gelatin-binding domain of fibronectin have been isolated and synthetically produced. The peptides can be used to bind to fibronectin or other related collagen-binding proteins to inhibit fibronectin-dependent cell adhesion to collagen matrices and to inhibit interactions with collagen of other proteins that share homologies with the gelatin-binding domain of fibronectin.

12 Claims, 6 Drawing Sheets

PEPTIDE INHIBITORS OF FIBRONECTIN AND RELATED COLLAGEN-BINDING PROTEINS

FIELD OF THE INVENTION

The present invention relates to peptides derived from a domain of thrombospondin mediating interaction of thrombospondin with fibronectin, which peptides bind specifically to fibronectin and inhibit fibronectin binding to collagen, as well as to pharmaceutical compositions containing these peptides, and methods for inhibiting fibronectin binding to collagen using these peptides.

BACKGROUND OF THE INVENTION

Thrombospondin is a multi-functional protein capable of interacting with numerous macromolecules, e.g. fibronectin (Lahav, et al., 1984, Cell 31:253–262; Lahav, et al. 1984, Eur. J. Biochem. 145:151–156), heparin (Lawler, et al. 1981, Thromb. Res. 22:267–279) and collagen (Lahav, et al. 1984, Cell 31:253–262, Mumby, et al., 1984 J. Cell. Biol. 98:646–652). All of these molecules are constituents of the extracellular matrix, suggesting that thrombospondin forms complexes with other matrix components following its deposition into the matrix.

Gelder and Brown reported that thrombospondin inhibits interactions of fibronectin with gelatin (Gelder, F. B. and Brown, S. T. 1987, J. Lab. Clin. Med. 110:548–557). Platelet thrombospondin and an unidentified but biologically similar plasma protein were shown to inhibit the gelatin-binding activity of fibronectin; however, the domains or sequences of thrombospondin responsible for the interaction remained unknown. The interactive region has been implicated to be a different site on fibronectin, than the fibrin binding domain (Homandberg, G. A. and Kramer-Bjerke, J. 1987, Thromb. Res. 48:329–335) and at least two distinct domains of thrombospondin have been shown to bind fibronectin (Dardik, R. and Lahaw, J. 1989, Eur. J. Biochem. 185:581–588). Fibronectin and heparin compete for binding to the 27 kDa fragment of thrombospondin suggesting that these two proteins share a common or closely oriented binding site within the N-terminal domain of thrombospondin. Thrombospondin has also been shown to disrupt focal contact adhesions of endothelial cells attached to a fibronectin matrix (Murphy-Ullrich, J. E., and Hook, M. 1989, J. Cell. Biol. 109:1309–1319). The mechanism of this effect is unknown, but inhibition of the activity of thrombospondin by sulfated polysaccharides suggested that the heparin-binding domain of thrombospondin is involved.

A number of biologically active peptides from thrombospondin have been identified and isolated. Two peptides, ArgGlyAspAla (Lawler, J. and Hynes, R. O. 1986, J.Cell Biol. 103:1635–1641) and ValThrCysGly (Prater, et al., 1991, J.Cell Biol. 112: 1031–1040) are proposed to be ligands for the interaction of thrombospondin with protein receptors on the cell surface. The thrombospondin peptide TrpSerProTrpSer (Guo, et al. 1992, Proc. Nat. Acad. Sci. USA, 89:3040–3044) binds to heparin and sulfatide. However, there are no known thrombospondin peptides that are capable of binding to fibronectin or related collagen binding proteins.

Fibronectin has been implicated in a variety of cell contact processes, including cell attachment and migration. Fibronectin interacts with collagen through the "gelatin binding domain" of fibronectin and this interaction between collagen and fibronectin is fundamental to the organization of extracellular matrices and the behavior of these cells on substrates (Vaberi, et al., 1978, Proc. Natl. Acad. Sci. USA, 75: 4944–4948). Fibronectin is essential for the attachment and migration of many cells, including various tumor and cancer cells.

Accordingly, there is a need for inhibitors of fibronectin that will bind to fibronectin or related collagen-binding proteins with high affinity. There is particularly a need for such inhibitors which will bind to fibronectin or related collagen-binding proteins to prevent the fibronectin-dependent cell adhesion to collagen matrices and to inhibit interaction with collagens of other proteins that share homologies with the gelatin-binding domain of fibronectin.

It is, therefore, an object of the present invention to provide highly effective peptides having sequences which bind specifically and with specific affinity to fibronectin or other proteins having homologies with the fibronectin gelatin-binding domain so as to inhibit fibronectin-dependent cell adhesion to collagen matrices and to inhibit interaction of other proteins having homologies with the fibronectin gelatin-binding domain with collagens.

It is a further object of the present invention to provide pharmaceutical compositions containing at least one peptide which has a high affinity to fibronectin or other protein having homologies with the fibronectin gelatin-binding domain.

It is yet another object of the present invention to provide a method for binding fibronectin or other proteins having homologies with the fibronectin gelatin-binding domain in a patient in need thereof.

These and other objects of the invention will become more apparent from the following description and preferred embodiments and the aid of the accompanying drawings.

BRIEF DESCRIPTION OF THE DRAWINGS

FIG. 2 is a graph of the specificity of inhibition of fibronectin binding to the thrombospondin peptide GlyGlyTrpSerHisTrp (SEQ ID NO:1) by synthetic peptides.

FIG. 7(A) is a bar graph of the inhibition of fibronectin-mediated carcinoma cell MDA 4355 adhesion to gelatin by peptides GlyGlyTrpSerHisTrp (SEQ ID NO:1); GlyGlyTrpSerLysTrp (SEQ ID NO:9) or TrpSerHisTrpSerPro (SEQ ID NO:2).

SUMMARY OF THE INVENTION

Figure 1:
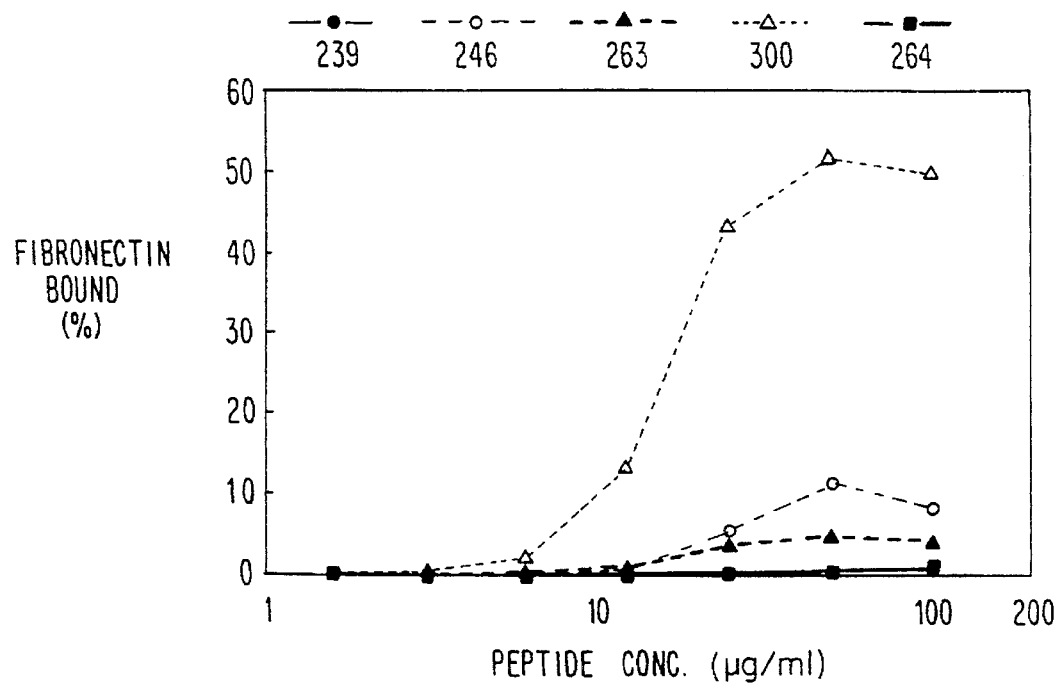
FIG. 1 is a graph of the binding of fibronectin to various immobilized thrombospondin peptides, i.e. SerHisTrpSerProTrpSerSer (SEQ ID NO:8) (●); LysArgPheLysGlnAspGlyGlyTrpSerHisTrpSerProTrpSerSer(SEQ ID NO:7) (o); LysArgPheLysGlnAspGlyGlyTrpSerHisTrpSerPro (SEQ ID NO:5) (▲); GlyGlyTrpSerHisTrp (SEQ ID NO:1) (Δ); and GlyGlyTrpSerHisTrpSerPro (SEQ ID NO:4) (■).

The present inventors have isolated, purified and characterized or synthesized and characterized biologically active peptides having a specific binding affinity for the gelatin-binding domain of fibronectin, which peptides have a sequence of at least five amino acids including the sequence HisTrp and at least one other tryptophan residue. In a preferred embodiment of the invention the peptide includes the sequence XaaHisTrp, wherein Xaa is an amino acid selected from serine, threonine and alanine. More preferably, the peptide has a sequence including the hexapeptide GlyGlyTrpXaaHisTrp, wherein Xaa is defined as above. In a particularly preferred embodiment of the invention, the peptide is a peptide having one of the sequences SEQ ID NO:1, SEQ ID NO:2, SEQ ID NO:3, SEQ ID NO:4, SEQ ID NO:5, SEQ ID NO:6, SEQ ID NO:7 and SEQ ID NO:8. Most preferred is the hexapeptide GlyGlyTrpSerHisTrp (SEQ ID NO:1).

In another aspect of the invention, there is provided a pharmaceutical composition for binding fibronectin or other related collagen-binding proteins which includes an effective amount of at least one peptide of the invention and a pharmaceutically acceptable excipient or carrier. In a preferred embodiment of the invention, the pharmaceutical composition includes an effective amount of one of the peptides selected from SEQ ID NO:1, SEQ ID NO:2, SEQ ID NO:3, SEQ ID NO:4, SEQ ID NO:5, SEQ ID NO:6, SEQ ID NO:7 and SEQ ID NO:8 and a pharmaceutically acceptable carrier or excipient. Most preferably, the pharmaceutical composition of the invention is the hexapeptide having sequence SEQ ID NO:1.

In another aspect of the invention, there is provided a method for binding fibronectin or other collagen-binding proteins in a patient in need of such treatment wherein an effective amount of peptide having a specific binding affinity for the gelatin-binding domain of fibronectin and which includes at least 5 amino acids, including the sequence HisTrp and at least one other tryptophan residue, is administered to such patient. In a preferred embodiment of the invention method, the peptide is a peptide having a sequence selected from SEQ ID NO:1, SEQ ID NO:2, SEQ ID NO:3, SEQ ID NO:4, SEQ ID NO:5, SEQ ID NO:6, SEQ ID NO:7 and SEQ ID NO:8. Most preferred is a method wherein the peptide is the hexapeptide SEQ ID NO:1.

The term "collagen-binding proteins" is used herein to describe proteins having a domain capable of specifically binding to or interacting with collagen.

The term "gelatin-binding domain of fibronectin" is used herein to describe the amino acid sequence of mammalian fibronectin which is the site of interaction of mammalian fibronectin with gelatin. The "gelatin" is used to define denatured collagen.

The term "specific binding affinity for fibronectin" is used herein to mean at least 1% by weight binding of fibronectin to peptides under saturating peptide conditions. The symbol (+) indicates binding of 1 to 5%, (++) indicates from more than 5 to 50% binding and (+++) indicates more than 50% binding to fibronectin.

The one letter codes for amino acids and the corresponding three letter codes which are used herein are as follows:
W=Trp
K=Lys
Y=Tyr
P=Pro
D=Asp
R=Arg
F=Phe
Q=Gln
E=Glu
T=Thr
G=Gly
S=Ser
A=Ala

DETAILED DESCRIPTION OF THE INVENTION

The peptides according to the invention are derived from the extra cellular matrix protein thrombospondin. In particular, the peptides are derived from one of the domains that mediate interaction of thrombospondin with the matrix adhesive protein fibronectin. The peptides of the present invention are derived from the second type 1 repeat of thrombospondin. Thrombospondin is a modular adhesive glycoprotein that contains three domains that have been implicated in the attachment of cells to thrombospondin. One region of thrombospondin, consisting of a chymotryptic 50 kDa peptide contains the three type 1 repeats of a 57 residue segment homologous to two malarial proteins (Lawler J. and Hynes, R. O. 1986, J. Cell. Biol. 103: 1635–1648). The amino acid sequence of the second type 1 repeat is incorporated herein by reference thereto.

The peptides of this invention interact directly with the gelatin-binding domain of fibronectin. The gelatin-binding domain of fibronectin is necessary for the interaction of fibronectin with gelatin. Specific and preferred sequences of the peptides of the invention are set forth in Table 1 and may be produced by any of a variety of art known methods. Such methods of peptide synthesis include, for example, solid phase peptide synthesis, genetic engineering techniques including the cloning of DNA encoding the peptide in an expression vector, and the direct isolation of the peptide from thrombospondin.

Table 1 also includes other peptides (FN Binding-) which while having homology to the peptides according to the invention (FN Binding +, ++, +++) do not include the essential His-Trp (H-W) sequence.

TABLE 1

Fibronectin binding to immobilized peptides.

| Peptide | Seq. Id No: | Sequence | FN Binding |
| --- | --- | --- | --- |
| 239 | 8 | SHWSPWSS | + |
| 246 | 7 | KRFKQDGGWSHWSPWSS | ++ |
| 256 | 6 | GGWSHWSPWSS | ++ |
| 259 | 17 | GGWSHASPWSS | – |
| 263 | 5 | KRFKQDGGWSHWSP | ++ |
| 266 | 27 | KRFKQDGGASHASP | – |
| 264 | 4 | GGWSHWSP | + |
| 285 | 3 | WSHWS | + |
| 292 | 2 | WSHWSP | + |
| 300 | 1 | GGWSHW | +++ |
| 322 | 28 | QDGGWS | – |
| 317 | 15 | DGWSPW | – |
| 318 | 21 | GGWGPW | – |
| 319 | 29 | GTWSEW | – |
| 320 | 30 | GFWSEW | – |

The peptides of the invention bind specifically to the gelatin-binding domain of fibronectin. The sequences responsible for fibronectin-binding of the present peptides are contained in a peptide previously identified as a heparin-binding peptide, however, the optimal sequence for binding fibronectin has only weak heparin-binding activity (U.S. application Ser. No. 07/801,812). More particularly, a 17 amino acid peptide (peptide 246) (SEQ ID NO:7) comprising part of the second type I repeat of thrombospondin (KRFKQDGGWSHWSPWSS) exhibits strong affinity for fibronectin and is a potent inhibitor of fibronectin binding to gelatin and of fibronectin-mediated cell adhesion to a gelatin matrix. Binding of the present peptides to fibronectin does not require the amino terminal basic residues of peptide 246, since peptide 256 (GGWSHWSPWSS) (SEQ ID NO:6) which lacks these residues also binds fibronectin.

At least two tryptophan residues in the correct position are required for binding. The central tryptophan residue of peptide 246 (SEQ ID NO:18) (residue 9) is required for binding since a similar peptide (259) lacking this tryptophan residue fails to bind (Table 1 and FIG. 1). Among overlapping peptides derived from the 17 amino acid peptide 246 (SEQ ID NO:7) the peptide having the sequence GlyGlyTrpSerHisTrp (SEQ ID NO:1) has strongest binding activity (FIG. 1 and Table 1). Most preferred among the peptides of the invention is the hexapeptide having the sequence GlyGlyTrpSerHisTrp (SEQ ID NO:1).

The peptides of the present invention may contain sequences derived from the consecutively occurring human thrombospondin amino acids. Preferably, the consecutively occurring amino acid sequences are selected from amino acids 394–420 and 424–450. Especially preferred are the consecutive amino acids 410–420 and 424–434.

Figure 2A:
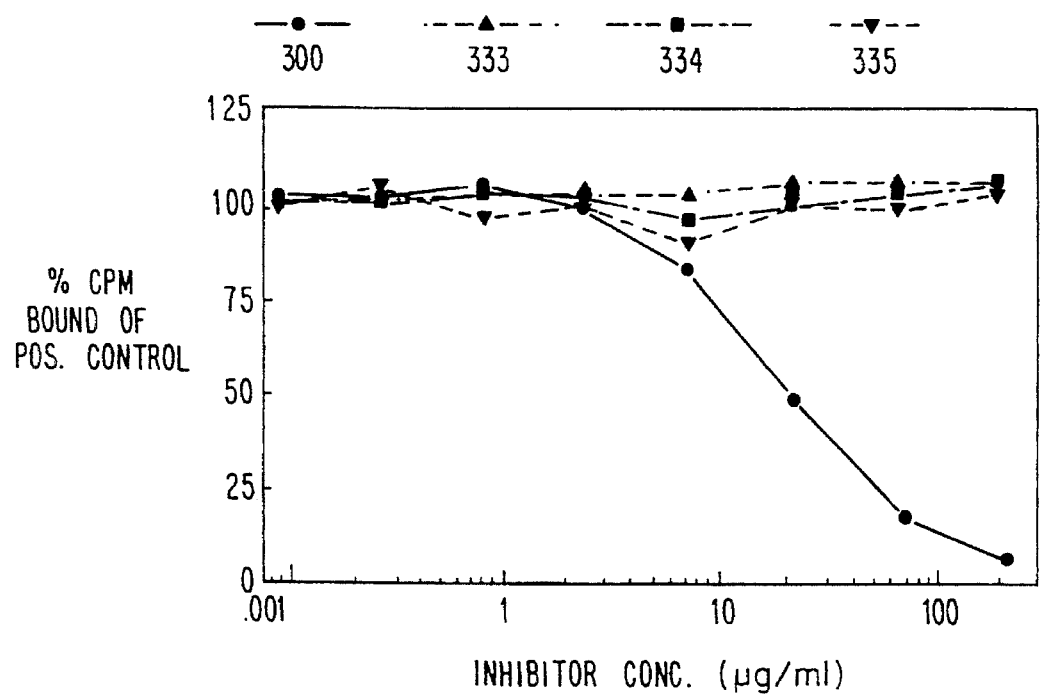
In FIG. 2(A) the peptides are GlyGlyTrpSerHisTrp (SEQ ID NO:1) (●); GlyGlyTrpSerLysTrp (SEQ ID NO:9) (▲); GlyGlyTyrSerHisTrp (SEQ ID NO:10) (■); and GlyGlyTrpSerHisTyr (SEQ ID NO:11) (▼)
Figure 2B:
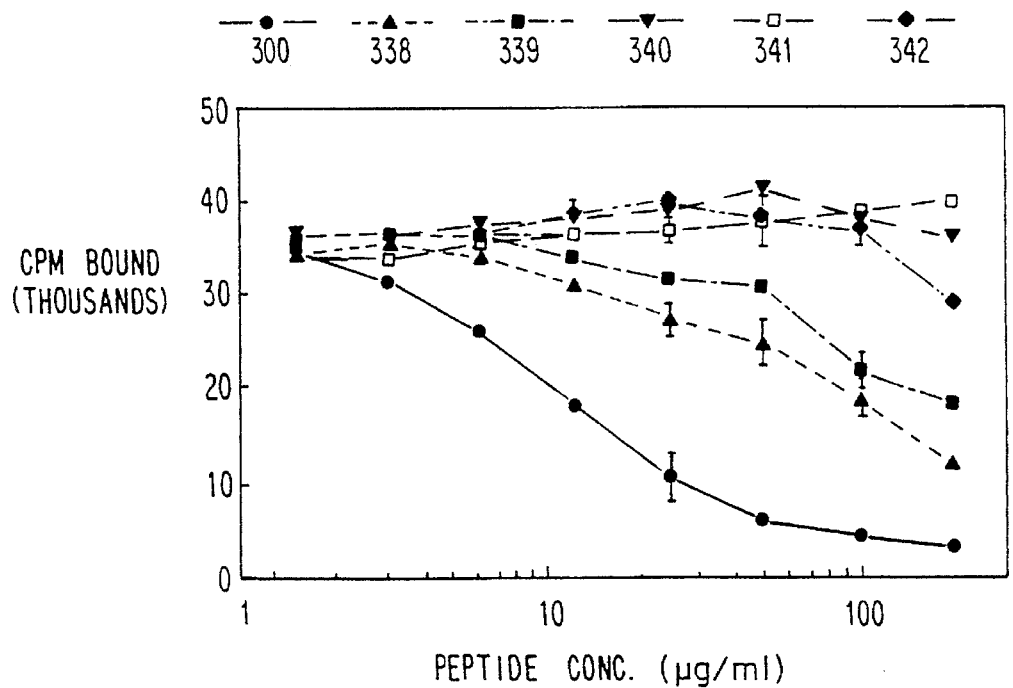
FIG. 2(B): GlyGlyTrpSerHisTrp (SEQ ID NO:1) (●); GlyGlyTrpThrHisTrp (SEQ ID NO:12) (▲); GlyGlyTrpAlaHisTrp (SEQ ID NO:13) (■); GlyTrpSerHisTrp (SEQ ID NO:14) (+) and AspGlyTrpSerHisTrp (SEQ ID NO:15) (□).

The binding activity of several peptides derived from the second Type 1 repeat of thrombospondin are shown in FIG. 1. At saturating peptide concentrations of 100 μg/ml, more than 50% of added fibronectin is bound to the immobilized peptides of this invention. The hexapeptide consisting of the peptide sequence GlyGlyTrpSerHisTpr (SEQ ID NO:1) binds fibronectin better than larger peptides containing the same sequence or intact thrombospondin, indicating that the 6 residue sequence is partially cryptic in thrombospondin. It is not necessary that the peptides of the invention contain the entire hexapeptide sequence for effective fibronectin binding however, it is necessary that the peptides share some sequence homology with the hexapeptide. Two tryptophan residues and the His residue of the hexapeptide are essential in the peptides of the invention since even conservative substitution with similar amino acids renders the peptides inactive (FIG. 2). Preferably, the serine residue is present but it is not essential. Optimal binding is obtained with peptides comprising the serine residue (FIG. 2B). Conservative substitution of the serine residue with a threonine residue decreases activity approximately five-fold and substitution of the serine residue with an alanine residue produces an active peptide having a slightly higher inhibition constant than the threonine analog. The presence of two glycine residues strongly enhances activity relative to a peptide analog having only one glycine residue (FIG. 2B). Conservative substitution of both glycine residues with alanine or of the first glycine residue with aspartic acid abolishes activity. Preferably, the peptide comprises two glycine residues, however, peptides lacking one or both glycine residues are within the scope of the invention.

Accordingly, the peptides of this invention have a sequence of at least 5 amino acids residues, which include at least two tryptophan residues, at least one of which is present as the sequence HisTrp (HW) wherein said peptide has specific binding affinity for the gelatin-binding site of fibronectin. More preferred is a peptide with at least 5 amino acid residues including the sequence XaaHisTrp, wherein Xaa is an amino acid selected from serine, threonine and alanine and wherein the 5 amino acids has at least two Trp residues. Even more preferred is the hexapeptide GlyGlyTrpXaaHisTrp, wherein xaa is serine, threonine or alanine.

In a particularly preferred embodiment of the invention, the peptide according to the invention is a peptide having a sequence independently selected from SEQ ID NO:1, SEQ ID NO:2, SEQ ID NO:3, SEQ ID NO:4, SEQ ID NO:5, SEQ ID NO:6, SEQ ID NO:7 and SEQ ID NO:8. Most preferable is the peptide SEQ ID NO:1.

The peptides of the present invention retain proper conformation in solution for binding to fibronectin with specific binding affinity. Moreover, the peptides of the present invention bind specifically to the gelatin-binding site of fibronectin and preferably, at least 5% binding affinity under saturating pending conditions. The present peptides are potent inhibitors of fibronectin binding to gelatin and of fibronectin-mediated cell adhesion to a gelatin matrix.

Fibronectin is an important extracellular matrix component that mediates cell interactions and extracellular matrix assembly during normal development. It also participates in homeostasis and wound healing, and peptides that inhibit fibronectin interactions with cells have been demonstrated to inhibit tumor metastasis in animal models (Humphries, M. J. Olden, K and Yamada, K., (1986) Science 233, 467–470).

The present peptides represent a new class of inhibitors of fibronectin function. The peptides of this invention bind specifically to fibronectin and inhibit interactions of fibronectin with collagen but not with cell surface integrin receptors for fibronectin. As such, these peptides are applicable in regulating cell matrix interactions involved in tumorigenesis, metastasis, wound repair and homeostasis. For example, the present peptides inhibit fibronectin-dependent adhesion of the human breast carcinoma cell line MDA-MB 435 to immobilized gelatin. The inhibition of adhesion of these cancer cells by the peptides of the present invention is specific in that a homologous peptide lacking fibronectin binding activity fails to inhibit adhesion (see FIGS. 6–A, 6–B and 7).

As noted above, only partial sequence homology with the hexapeptide GlyGlyTrpSerHisTrp (SEQ ID NO:1) is needed to inhibit fibronectin binding to gelatin. The existence of homologous sequences comprising active sites in various proteins suggests that the activities of other proteins containing domains homologous to the fibronectin gelatin-binding domain can be regulated with the peptides of the present invention. For example, such proteins as matrix metalloproteinase-2 and matrix metalloproteinase share homology with the fibranectin gelatin-binding domain and, therefore, may be regulated by the peptides of this invention.

There is a high degree of conservation of the fibronectin-binding hexapeptide GlyGlyTrpSerHisTrp (SEQ ID NO:1) in the thrombospondin gene family. The sequence is completely conserved in the second type I repeats of mouse and human Thbs1 genes and in Thbs 2 genes from mouse and chicken (Laherty, et al. 1992, J. Biol. Chem. 267: 3274–3281). A search of the Swiss-Prot data base using the search sequence GlyGlyTrpSerHisTrp (SEQ ID NO:1) yielded several other proteins with similar sequences. (see Table II). Epstein-Barr virus ribonucleotide reductase contains the most homologous sequences, GlyGlyTrpPheHisTrp (SEQ ID NO:18). The α-subunit of the nicotinic acetylcholine receptor, which is highly conserved among vertebrate acetylcholine receptor sequences also shares sequence homology with the hexapeptide through the sequence GlyTrpLysHisTrp (SEQ ID NO: 19). A peptide of acetylcholine receptor containing the sequence GlyTrpLysHisTrp (SEQ ID NO:19) plays a role in acetylcholine binding to the receptor. Furthermore another similar sequence, TrpSerXTrpSer, has been identified as a potential "binding" sequence (Miyazaki, et al. 1991; Embo J. , 3191–3197; Yoshimura, et al. 1992, J. Biol. Chem. 267: 11619–11625). The ligands that interact with this site have not been identified, but loss of receptor processing or activity following mutation of the consensus sequence suggests that cellular factors involved in protein folding, intracellular processing, or signal transduction are potential ligands.

TABLE II

Amino acid sequence homologies with the fibronectin-binding sequence from thrombospondin.

| Source | Sequence |
| --- | --- |
| human Thbs1 | KRFKQDGGWSHWSPWSSC |
| mouse Thbs1 | KRFKQDGGWSHWSPWSSC |
| mouse Thbs2 | TRIRQNGGWSHWSPWSSC |
| chicken Thbs2 | HRIRQDGGWSHWSPWSSC |
| EBV ribonucleotide reductase | KQSKYAGGWSHWHDWAGC |
| chicken AchR | WVMKDYRGWKHWVYYACC |
| T. California AchR | WVMKDYRGWKHWVYYTCC |
| rat AchR | WVIKEARGWKHWVFYSCC |
| mouse AchR | WVIKEARGWKHWVFYSCC |
| bovine AchR | WVIKESRGWKHWVFYACC |

Sequence identity with the thrombospondin sequence is indicated by bold residues.

Compositions containing a therapeutically effective amount of at least one peptide of the present invention are prepared by any methods known in the art. For example, the compositions are prepared by forming an admixture of at least one peptide of the present invention and a pharmaceutically acceptable carrier or excipient, such as for example, sterile saline, Ringers solution, Ringer's lactate or 5% dextrose. The peptides may be mixed with a variety of carrier compounds depending on the form of preparation desired for administration.

In another embodiment, the peptides of the present invention may be conjugated with a suitable carrier polymer or protein. For example, chemical conjugation to the peptide can be used to target specific cells by attachment to an antibody against a surface protein of the target cell.

Various methods of administration of peptides are known to those skilled in the art. Such methods of administration may include, but are not limited to, surface application, oral and parenteral routes, injection into joints, subcutaneous injection via sustained release, intravenous injection or other pharmaceutical methods of delivery.

Appropriate dosages of the peptides of the invention will depend upon the condition presented by the individual subject. The skilled medical worker will be able to determine appropriate dosages required to combat the physiological activity. However, in general, amounts of from about 1 µg to 100 µg/kg body weight/day of the biologically active peptide should be useful.

The following examples are provided to more fully illustrate the principles and practices of the invention. The examples are not intended in any way to limit the scope of the invention.

EXAMPLE 1

This example illustrates the binding of peptides of the invention to fibronectin.

Fibronectin was isolated from platelet-depleted plasma as described (Ariyama, et al. 1985, J. Biol. Chem. 260:4492–4500) and iodinated using Iodogen (Pierce Chemical Co., Rockford, Ill.) as described (Roberts, et al. 1987, J. Cell. Biol. 104:131–139).

Peptides were synthesized corresponding to sequences of human thrombospondin deduced from a cDNA sequence for human endothelial cell thrombospondin (C Lawler and Hynes, 1986, J. Cell. Biol. 103:1635–1648). Peptides were synthesized on a Biosearch Model 9600 peptide synthesizer using standard Merrifield solid phase synthesis protocols and t-Boc chemistry. Peptides were analyzed and where necessary, further purified by reverse-phase HPLC chromatography. Identities of some of the peptides, including peptide 246 (SEQ ID NO:7), were verified by complete amino acid sequence analysis. Peptide solutions were neutralized by addition of dilute NaOH and stored in solution at −20° C.

Direct binding of the fibronectin to immobilized peptides was carried out by first absorbing the peptides on polyvinyl chloride microtiter wells for 3 hours at 25° C. at the indicated concentrations. Unbound peptides were removed by washing and wells were incubated for 30 minutes in tris-BSA (50 mMtris-HCl, pH7-8, 110mmNaCl, 1% BSA) (Sigma fatty acid and globulin-free, 0.1% $NAN_3$). The wells were washed and incubated with 30 ml of 0.5 µg/ml $^{125}$I-fibronectin for 2 hours at 25° C. The wells were washed five times with Dulbecco's phosphate buffered saline and cut from the plate and bound radioactivity was counted.

The peptides listed in Table 1 were synthesized as described above and absorbed to microtiter wells. Of the larger peptides tested from the type I repeats or the carboxyl terminal domain of thrombospondin, only peptide 246 (SEQ ID NO:7) bound labelled fibronectin. The peptide GlyGlyTrpSerHisTrp (SEQ ID NO:1) exhibited the strongest binding activity. This peptide sequence is located in the second type I repeat of the human ThbsI gene. Synthetic peptides 317 (SEQ ID NO:15) and 318 (SEQ ID NO:20), derived from the corresponding positions in the first and third type I repeats of thrombospondin were inactive.

The results are shown in Table 1 and FIG. 1. FIG. 1 shows binding of I-fibronectin to peptides 300 (Δ) (GlyGlyTrpSerhisTrp) (SEQ ID NO:1); 246 (o) (LysArgPheLysGlnAspGlyGlyTrpSerHisTrpSerProTrpSerSer) (SEQ ID NO:7); 263 (▲) (LysArgPheLysGlnAspGlyGlyTrpSerHisTrpSerPro) (SEQ ID NO:5) (■) and 264 (GlyGlyTrpSerHisTrpSerPro) ( SEQ ID NO:4 ).

EXAMPLE 2

This example illustrates the specificity of inhibition of fibronectin binding to thrombospondin peptide 300 (GlyGlyTrpSerHisTrp) by synthetic peptides.

Microtiter plate wells were coated with 50 μg/ml of peptide GlyGlyTrpSerHisTrp (SEQ ID NO:1) as in Example 1. Binding of $^{125}$I-fibronectin (0.5 μg/ml) to bound peptide was determined in the presence of increasing amounts of the peptides: Panel A: the peptides are GlyGlyTrpSerHisTrp ( SEQ ID NO:1) (●); GlyGlyTrpSerLysTrp (SEQ ID NO:9) (▲); GlyGlyTyrSerHisTrp ( SEQ ID NO:10) (■) and GlyGlyTrpSerHisTyr (SEQ ID NO:11) (▼); Panel B: GlyGlyTrpSerHisTrp (SEQ ID NO:1) (●); GlyGlyTrpThrHisTrp (SEQ ID NO:12) (▲); GlyGlyTrpAlaHisTrp (SEQ ID NO:13) (■); GlyTrpSerHisTrp (SEQ ID NO:14) (+); AlaAlaTrpSerHisTrp (SEQ ID NO:21) (▼); and AspGlyTrpSerHisTrp (SEQ ID NO:22) (□) .

The results are shown in FIG. 2.

Binding of fibronectin to immobilized peptide GlyGlyTrpSerHisTrp (SEQ ID NO:1) was inhibited by soluble peptide 300 with 50% inhibition at 27 μm. Three hexapeptides containing conservative single amino acid substitutions, GlyGlyTrpSerLysTrp (SEQ ID NO:9); GlyGlyTyrSerHisTrp (SEQ ID NO:10) and GlyGlyTrpSerHisTyr (SEQ ID NO:11) were inactive. The corresponding hexapeptides from the first and third repeats of thrombospondin were also inactive.

EXAMPLE 3

This example illustrates the inhibition of fibronectin binding to thrombospondin peptide GlyGlyTrpSerHisTrp by soluble fibronectin, thrombospondin and synthetic peptide GlyGlyTrpSerHisTrp.

Human platelet thrombospondin was purified according to the method of Roberts, et al. 1985 J. Cell Biol. 104:131–139.

Figure 3:
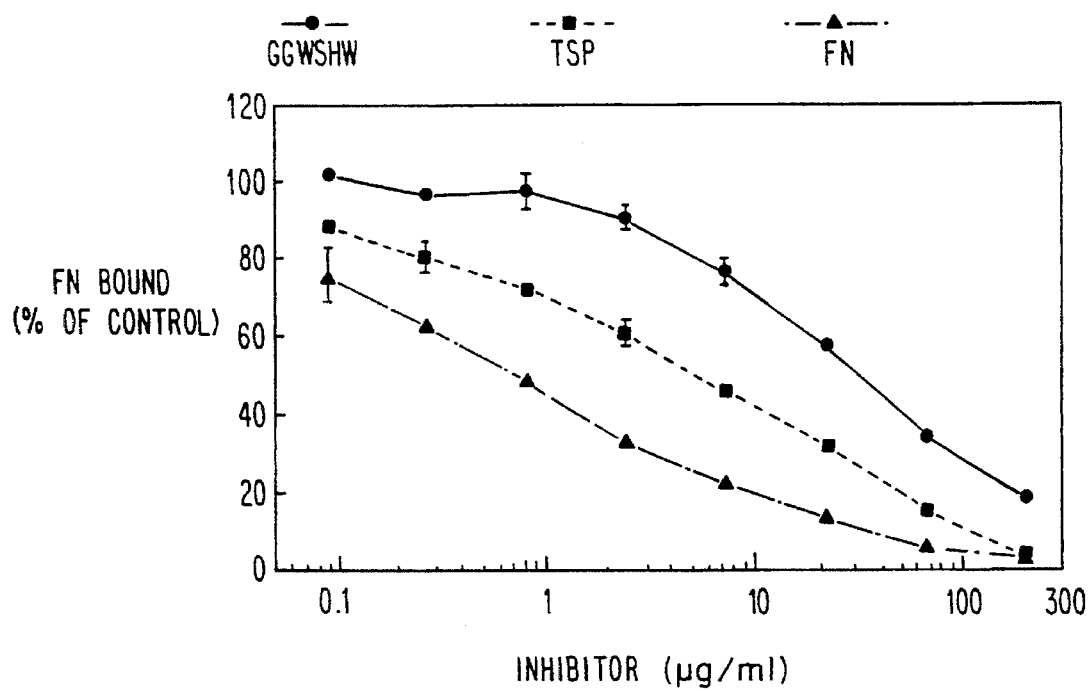
FIG. 3 is a graph of the inhibition of fibronectin binding to thrombospondin peptide GlyGlyTrpSerHisTrp by soluble fibronectin, thrombospondin and peptide GlyGlyTrpSerHisTrp (SEQ ID NO:1), GlyGlyTrpSerHisTrp (SEQ ID NO:1) (●), fibronectin (▲) and thrombospondin (■).

Binding of $^{125}$I-fibronectin (0.5 μg/ml) to microtiter plate wells coated with 50 μg/ml of peptide GlyGlyTrpSerHisTrp (SEQ ID NO:1) was determined in the presence of synthetic peptide GlyGlyTrpSerHisTrp (SEQ ID NO:1), fibronectin or thrombospondin. The results are shown in FIG. 3.

Unlabelled fibronectin and thrombospondin competed for binding of $^{125}$I-fibronectin to the peptide GlyGlyTrpSerHisTrp (SEQ ID NO:1), but several control proteins, i.e. ovalbumin, transferrin, fetuin, goat IgG and murine laminin did not (IC$_{50}$>200 μg/ml).

EXAMPLE 4

This example illustrates that peptides of the present invention and whole thrombospondin bind to the gelatin-binding domain of fibronectin.

Figure 4:
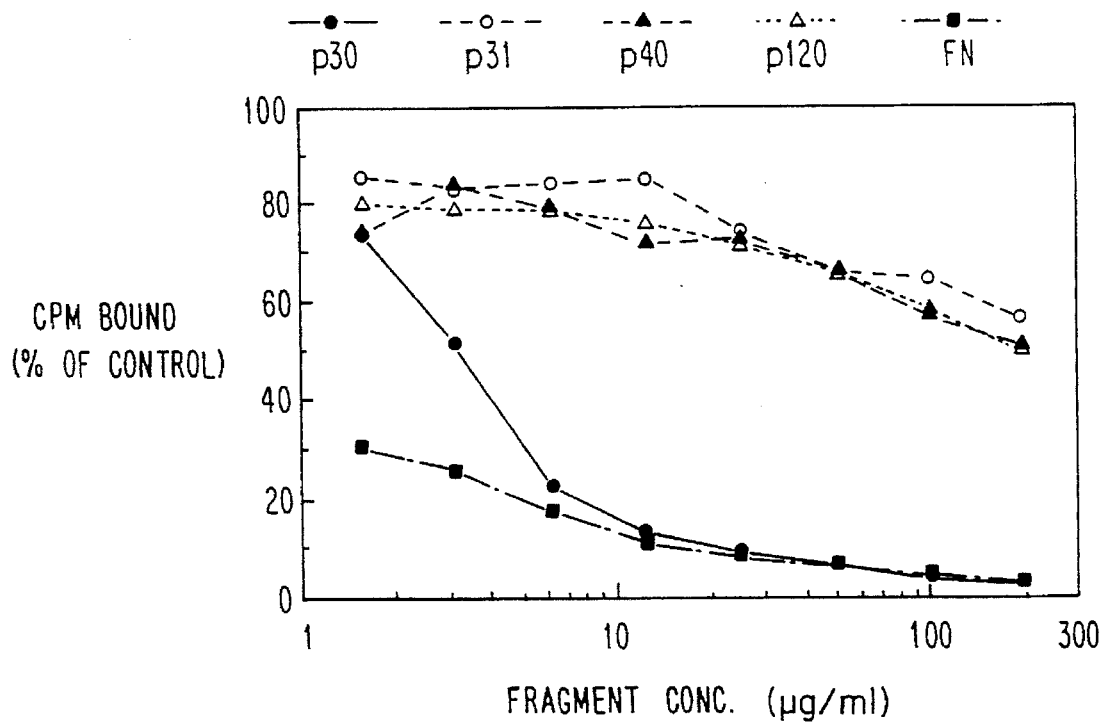
FIG. 4 is a graph of the inhibition of fibronectin binding to thrombospondin peptide GlyGlyTrpSerHisTrp by proteolytic fragments of fibronectin: 30 kDa gelatin-binding domain (●), 31 kDa fibrin-binding domain (o), 40 kDa heparin-binding domain (▲), 120 kDa cell-binding domain (Δ) and intact fibronectin (■).

Microtiter plates were coated with 50 μg/ml of synthetic peptide GlyGlyTrpSerHisTrp (SEQ ID NO:1) as described in Example 1. Binding of $^{125}$I-fibronectin (0.5 μg/ml) to the bound peptide was determined in the presence of proteolytic fragments of fibronectin, which were obtained from Telios Pharmaceuticals, Inc. San Diego, Calif. The proteolytic fragments included intact fibronectin; 30 kDa gelatin-binding domain; 33 kDa recombinant cell binding domain; 28 kDa recombinant cell binding domain and transferrin. The results are shown in FIG. 4.

Of the proteolytic fragments tested, the gelatin-binding domain was the strongest inhibitor of $^{125}$I-fibronectin binding to immobilized peptide. The 33 kDa fragment, which contains the cell binding domain was inhibitory. However, the 28 kDa fragment which contains all but the N-terminal 5 kDa of the 33 kDa fragment was inactive and a 40 kDa fragment with the same amino terminus as the 28 kDa fragment was approximately 10-fold less active. Since the sequence of the 33 kDa recombinant fragment is contained in the 120 kDa fragment of fibronectin and the 120 kDa fragment was only a weak inhibitor, the activity expressed by the 33 kDa fragment is probably due to a cryptic site. The activity of the 33 kDa fragment is less than that of the gelatin binding fragment.

EXAMPLE 5

This example illustrates the .specificity of inhibition of fibronectin binding to gelatin by the peptide GlyGlyTrpSerHisTrp.

Figure 5:
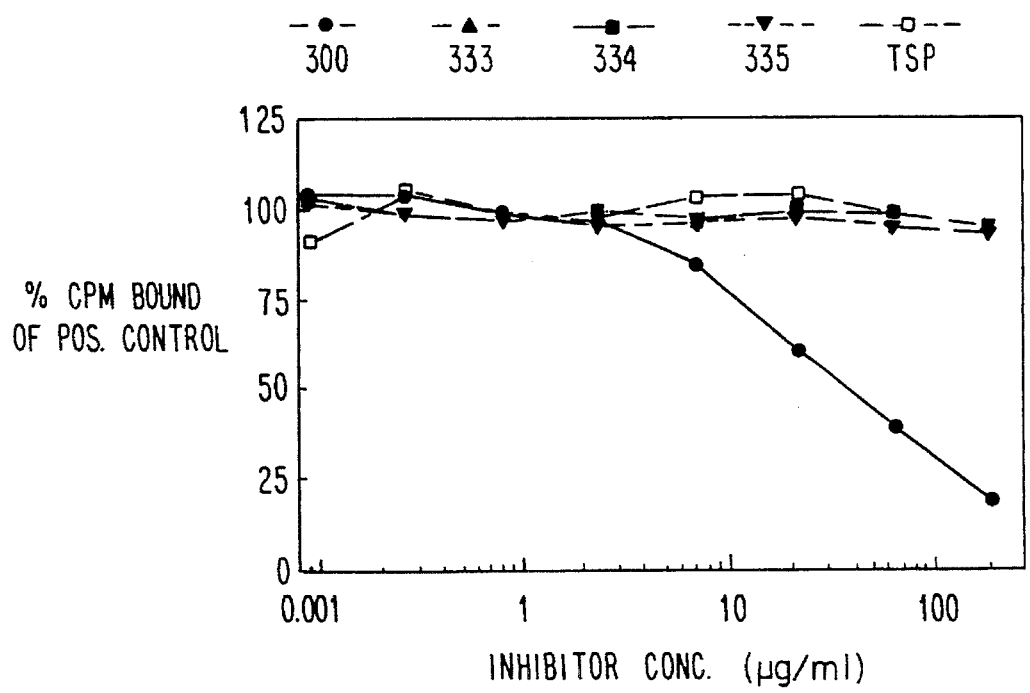
FIG. 5 is a graph of the inhibition of fibronectin binding to gelatin by peptide GlyGlyTrpSerHisTrp (SEQ ID NO:1).

Wells of a microtiter plate were incubated for 3 hours at 25° C. with 2 μg/ml gelatin in Dulbecco's PBS. The wells were emptied and incubated with Dulbecco's PBS containing 1% BSA for 30 minutes. The wells were emptied and incubated with 0.5 μg/ml $^{125}$I-fibronectin in the presence of peptide GlyGlyTrpSerHisTrp (SEQ ID NO:1) (●); GlyGlyTrpSerLysTrp (SEQ ID NO:9) (▲); GlyGlyTyrSerHisTrp (SEQ ID NO:10) (■); or GlyGlyTrpSerHisTyr (SEQ ID NO:11) (▼) for 2 hours at 25° C. The wells were washed 4 times with PBS, cut from the plate and the bound radioactivity was counted. The results are shown in FIG. 5.

The inhibition by peptide GlyGlyTrpSerHisTrp (SEQ ID NO:1) was specific in that the related peptides GlyGlyTrpSerLysTrp (SEQ ID NO:9); GlyGlyTyrSerHisTrp (SEQ ID NO:10) and GlyGlyTrpSerHisTyr (SEQ ID NO:11), with single amino acid substitutions from the active sequence were inactive.

EXAMPLE 6

A ligand binding assay as described in Example 5 was performed except that microtiter plates were coated with immobilized native type I collagen in place of gelatin.

The peptide GlyGlyTrpSerHisTrp (SEQ ID NO:1) inhibited fibronectin binding to type I collagen with an IC$_{50}$=40 μm. GlyGlyTrpAlaHisTrp (SEQ ID NO:13) was a weak inhibitor and the peptides TrpSerHisTrpSerPro (SEQ ID NO:2); GlyGlyTrpSerLysTrp (SEQ ID NO:9); GlyGlyTyrSerHisTrp (SEQ ID NO:10); GlyGlyTrpSerHisTyr (SEQ ID NO:11); AlaAlaTrpSerHisTrp (SEQ ID NO:21); AspGlyTrpSerHisTrp (SEQ ID NO:22); and GlyGlyTrpThrHisTrp (SEQ ID NO:24) were inactive.

EXAMPLE 7

This example illustrates the inhibition of fibronectin-dependent cell adhesion to denatured collagen by peptide GlyGlyTrpSerHisTrp (SEQ ID NO:1).

Gelatin (1 μg/ml) in Dulbecco's PBS was coated on plastic discs in 24 well plates and incubated for 2 hours at 37° C. After the supernatant was removed, the discs were treated with 1% BSA-tris pH 7.8 for 30 minutes at ambient temperature. The discs were washed twice with PBS and 0.4 ml of RPM1 1640 medium containing 0.1% BSA and 1 µg/ml fibronectin and 2, 20 or 200 µg of the inhibitory peptides were added to the wells. A suspension of $10^5$ cells in 0.1 ml RPMI medium containing 0.1% BSA was added to the wells and incubated at 37° C. with 5% $CO_2$ for 1 hour. The discs were washed to remove nonadherent cells and stained. Adherent cells were counted microscopically. The results are shown in FIGS. 6 and 7.

Figure 6A:
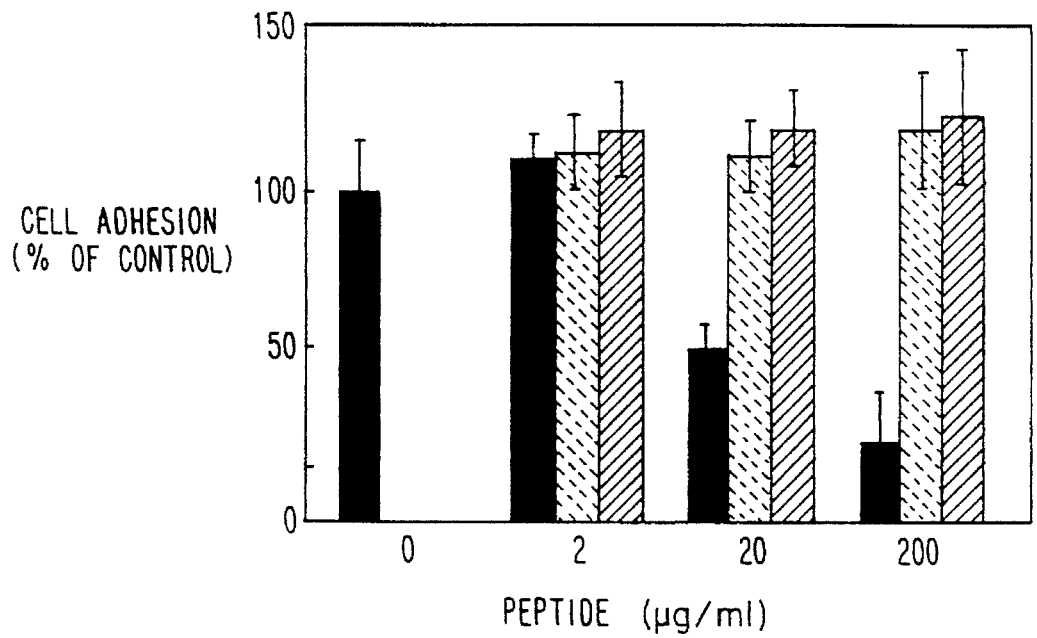
FIG. 6(A) is a bar graph of the inhibition of fibronectin-mediated melanoma cell A2058 adhesion to gelatin by peptides GlyGlyTrpSerHisTrp (SEQ ID NO:1) (●); GlyGlyTrpSerLysTrp (SEQ ID NO:9) or TrpSerHisTrpSerPro (SEQ ID NO:2).
Figure 6B:
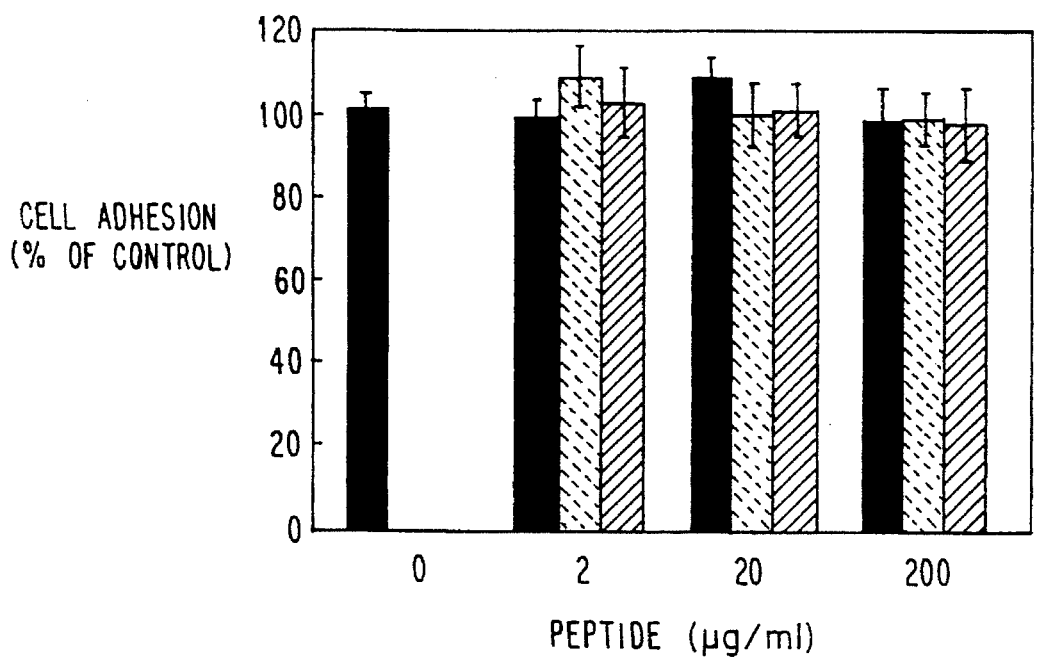
FIG. 6(B) is a bar graph of the inhibition of direct adhesion of A2058 cells to immobilized fibronectin by the peptides of this invention.
Figure 7B:
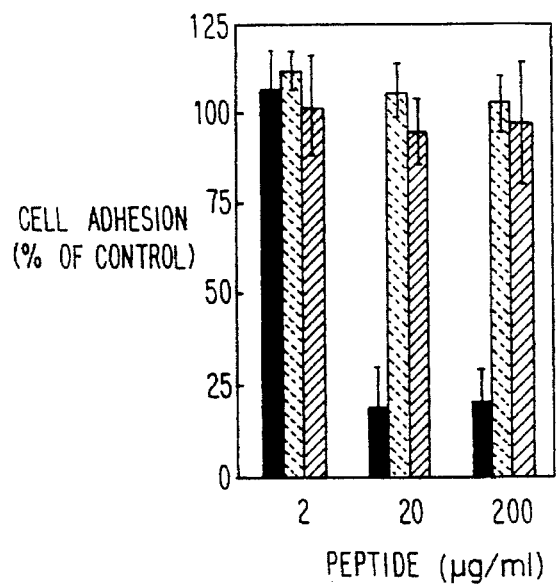
FIG. 7(B) is a bar graph of the inhibition of direct adhesion of MDA 435s cells to fibronectin by the peptides.
Figure 7B:
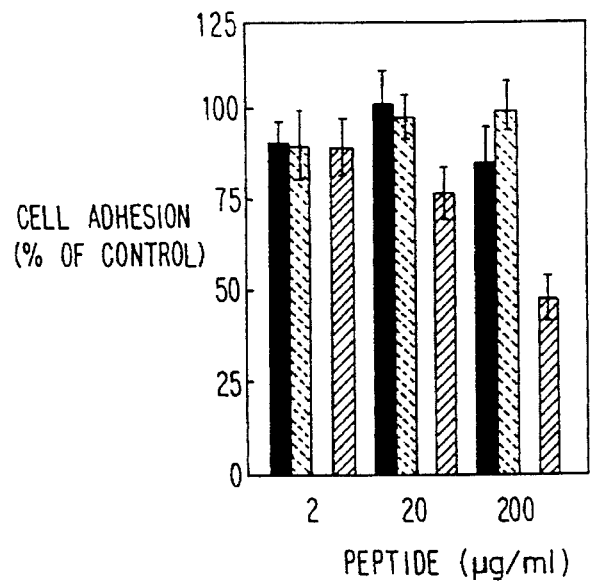
Figure 7B:
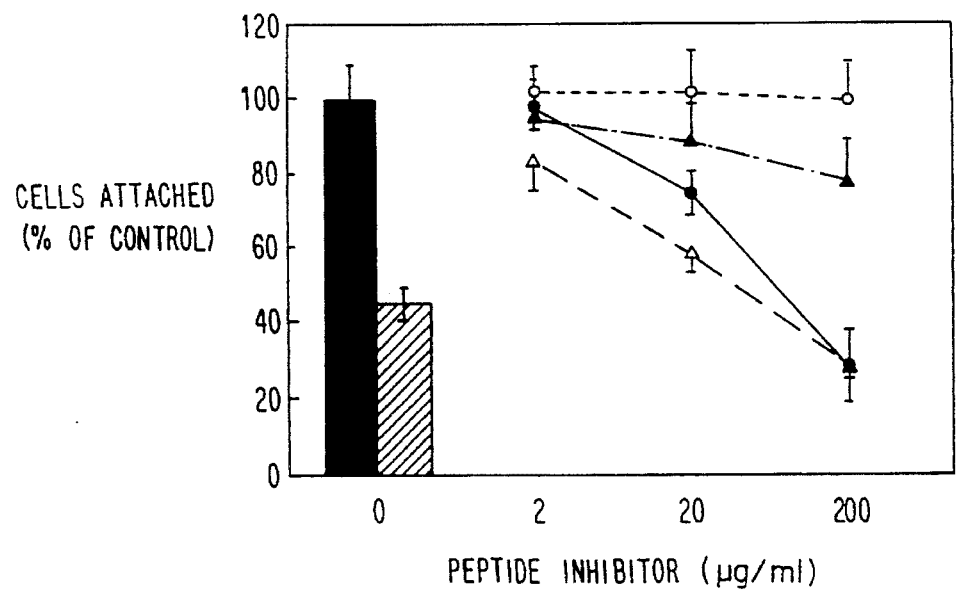

In panel A of FIG. 6 human melanoma cell of cell line A2058 were added to the wells and in Panel A of FIG. 7 MDA 435s breast carcinoma cells were added to immobilized gelatin. At the concentrations used, the cells weakly adhered to gelatin in the absence of added fibronectin. The stimulated adhesion in the presence of fibronectin was inhibited in a dose-dependent manner by the peptide GlyGlyTrpSerHisTrp (SEQ ID NO:1). The inhibition was specific in that the homologous peptides that lacked fibronectin binding activity, GlyGlyTrpSerLysTrp (SEQ ID NO:9) and TrpSerHisTrpSerPro (SEQ ID NO:2), were inactive.

Direct adhesion of A2058 cells (FIG. 6B) or MDA 435s cells (FIG. 7B) to immobilized fibronectin was not inhibited by the peptide GlyGlyTrpSerHisTrp (SEQ ID NO:1) or the control peptides, but adhesion of the breast carcinoma cells to fibronectin was inhibited by the peptide GlyArgGlyAspSer (SEQ ID NO:25). Thus, interaction of fibronectin with integrin receptors on the breast carcinoma cells is not inhibited by the peptide GlyGlyTrpSerHisTrp (SEQ ID NO:1).

EXAMPLE 8

This example illustrates the inhibition of fibronectin-mediated adhesion of breast carcinoma cells to native type I collagen by peptide GlyGlyTrpSerHisTrp (SEQ ID NO:1).

Figure 8:
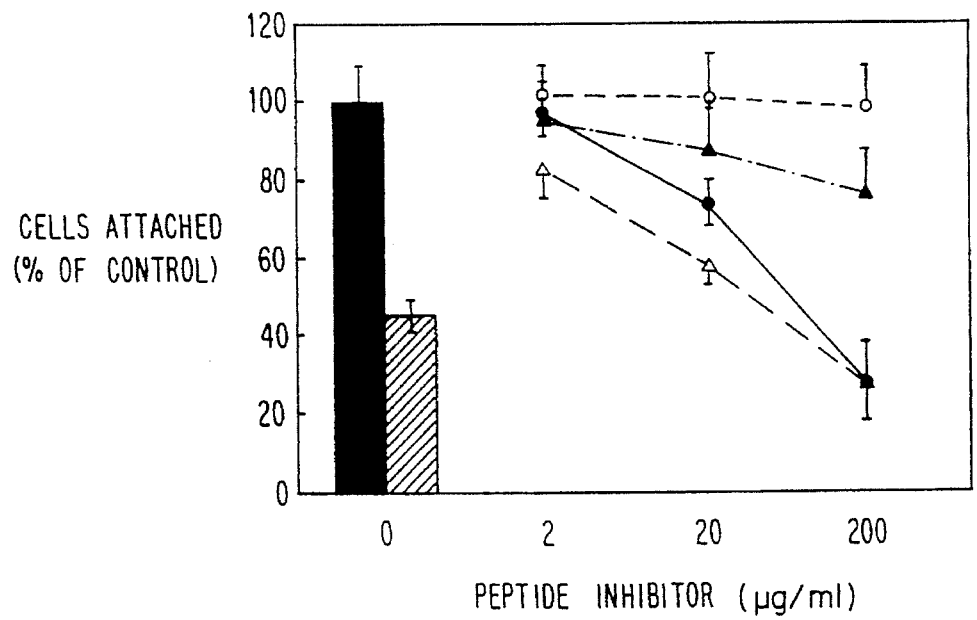
FIG. 8 is a graph of the inhibition of fibronectin-mediated adhesion of breast carcinoma cells MDA 435s to native type 1 collagen by peptide GlyGlyTrpSerHisTrp (SEQ ID NO:1); GlyGlyTrpSerLysTrp (SEQ ID NO:9); TrpSerHisTrpSerPro (SEQ ID NO:2) or GlyArgGlyAspSer (SEQ ID NO:16).
Figure 9:
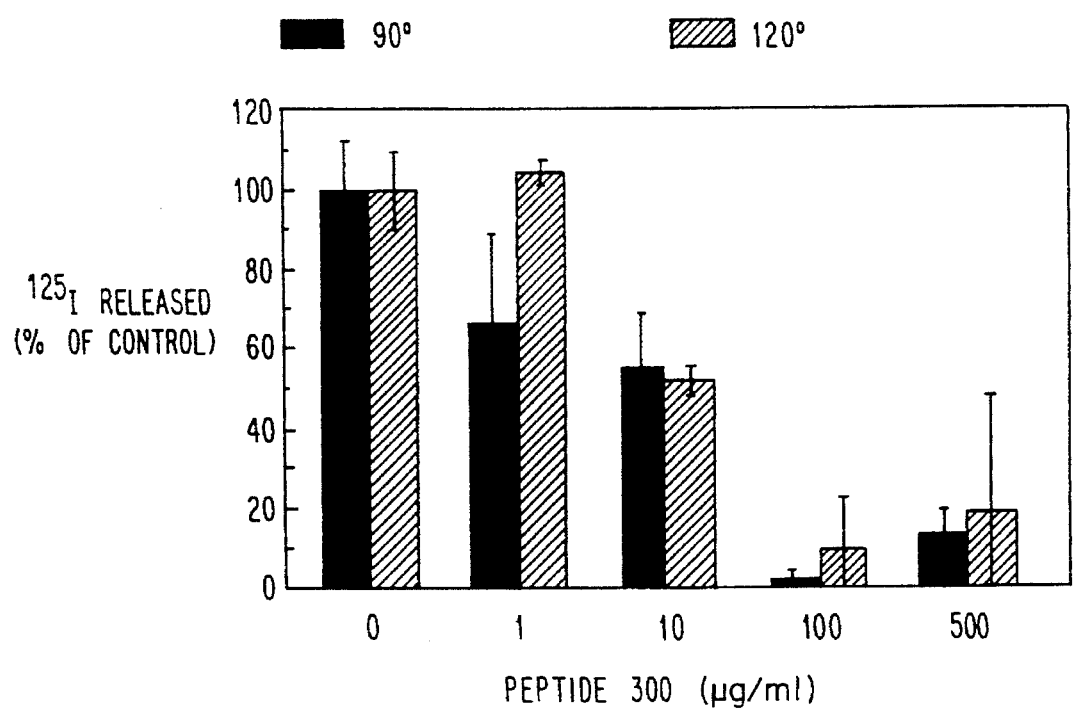
FIG. 9 is a bar graph of the inhibition of gelatinase activity by peptide (SEQ ID NO:1).

Discs were treated as in Example 7 except that 1 µg/ml of type I collagen in Dulbecco's PBS was coated on the discs. Cell attachment of breast carcinoma cells (cell line MDA 435s) to immobilized type I collagen was determined in the presence of fibronectin alone and in the presence of peptide GlyGlyTrpSerHisTrp (SEQ ID NO:1); GlyGlyTrpSerLysTrp (SEQ ID NO:9); TrpSerHisTrpSerPro (SEQ ID NO:2) or GlyArgGlyAspSer (SEQ ID NO:25). The results are shown in FIG. 8.

Fibronectin-mediated adhesion of breast carcinoma cells to native type 1 collagen was inhibited by peptides GlyGlyTrpSerHIsTrp (SEQ ID NO:1) and GlyArgGlyAspSer (SEQ ID NO:25) but not GlyGlyTrpSerLysTrp (SEQ ID NO:9) or TrpSerHisTrpSerPro (SEQ ID NO:2). Direct adhesion to type 1 collagen was stronger than to gelatin. The effects of the peptide GlyGlyTrpSerHisTrp (SEQ ID NO:1) were specific for fibronectin-stimulated adhesion, however, this peptide does not inhibit direct binding of cells to type 1 collagen.

EXAMPLE 9

This example illustrates inhibition of gelatinase by peptide GlyGlyTrpSerHisTrp. Degradation of $^{125}$I-gelatin by gelatinase activity in conditioned medium from bovine corneal endothelial cells was determined by release of radioactivity from microtiter plate wells coated with the radiolabeled substrate and incubated for 60 or 90 min with conditioned medium activated using p-hydroxymercuribenzoate. Activity in the presence of the indicated concentrations of peptide GlyGlyTrpSerHisTrp (SEQ ID NO:1) is presented as a percent of control activity determined in the absence of peptide and corrected for background release determined in the absence of mercurial activation. Inhibition was also determined by a gelatin zymogram of endothelial cell conditioned medium: a, control; b, 50 µg/ml GlyGlyTrpSerHisTrp (SEQ ID NO:1); c, 500 µg/ml GlyGlyTrpSerHisTrp (SEQ ID NO:1); d, 50 µg/ml GlyGlyTrpSerLysTrp (SEQ ID NO:9); e, 500 µg/ml GlyGlyTrpSerLysTrp; and f, 500 µg/ml peptide LysArgPheLysGlnAspGlyGlyTrpSerHisTrpSerProTrpSerSer(SEQ ID NO:7).

What is claimed is:

1. A method for binding fibronectin comprising contacting fibronectin with an effective amount of a composition comprising a peptide having a specific binding affinity for the gelatin-binding domain of fibronectin, said peptide having from 3 to 18 amino acids in length and consisting of the sequence (A), Xa—Xb—His—Trp—Xc,    (A)

wherein Xa is H or an amino acid sequence of from 1 to 13 amino acids derived from the consecutively occurring thrombospondin amino acid residues 394–420, Xb is serine, alanine, tryptophan, or threonine and Xc is OH, $NH_2$, or an amino acid sequence of from I to 13 amino acids derived from the consecutively occurring human thrombospondin amino acid residues 424–450, and at least one of Xa and Xb includes a tryptophan residue located within three amino acid residues from Trp in sequence (A).

2. A method according to claim 1 wherein said method is conducted in vitro or in vivo.

3. A method according to claim 1 wherein said method is conducted in vitro.

4. A method according to claim 1 wherein said method is conducted in vivo.

5. A method according to claim 4 wherein said method is conducted in a patient.

6. A method for binding fibronectin, according to claim 5, wherein said peptide is a peptide having a sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

7. A method for inhibiting enzymatic activity of collagenase in a patient in need of such treatment, which comprises administering to said patient an effective amount of at least one peptide contained in a pharmaceutically acceptable excipient or carrier, wherein said peptide is a peptide having a sequence selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

8. A method according to claim 5 wherein Xb is selected from the group consisting of serine, alanine and tryptophan.

9. The method according to claim 7 wherein said collagenase is endothelial collagenase.

10. A method according to claim 6 wherein said peptide is a peptide having SEQ ID No:1.

11. A peptide composition having a specific binding affinity for fibronectin, consisting essentially of a peptide selected from the group consisting of peptides having SEQ ID NO:1, SEQ ID NO:12 and SEQ ID NO:13.

12. A method according to claim 10, wherein said peptide further comprises an amino-terminal N-acetyl and carboxyl terminal amide.

* * * * *

SEQUENCE LISTING ( 1 ) GENERAL INFORMATION:

( i i i ) NUMBER OF SEQUENCES:30

( 2 ) INFORMATION FOR SEQ ID NO: 1:

( i ) SEQUENCE CHARACTERISTICS:
        ( A ) LENGTH:6 amino acids
        ( B ) TYPE:amino acid
        ( C ) TOPOLOGY:linear ( i i ) MOLECULE TYPE:Peptide ( x i ) SEQUENCE DESCRIPTION:SEQ ID NO:1:

Gly Gly Trp Ser His Trp
        1                 5

( 2 ) INFORMATION FOR SEQ ID NO: 2:

( i ) SEQUENCE CHARACTERISTICS:
        ( A ) LENGTH:6 amino acids
        ( B ) TYPE:amino acids
        ( C ) TOPOLOGY:linear ( i i ) MOLECULE TYPE:peptide ( x i ) SEQUENCE DESCRIPTION:SEQ ID NO: 2:

Trp  Ser  His  Trp  Ser  Pro
    1                       5

( 2 ) INFORMATION FOR SEQ ID NO: 3:

( i ) SEQUENCE CHARACTERISTICS:
        ( A ) LENGTH:5 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 3:

Trp  Ser  His  Trp  Ser
    1                       5

( 2 ) INFORMATION FOR SEQ ID NO: 4:

( i ) SEQUENCE CHARACTERISTICS:
        ( A ) LENGTH:8 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 4:

Gly  Gly  Trp  Ser  His  Trp  Ser  Pro
    1                       5

( 2 ) INFORMATION FOR SEQ ID NO: 5:

( i ) SEQUENCE CHARACTERISTICS:
        ( A ) LENGTH:14 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 5:

Lys  Arg  Phe  Lys  Gln  Asp  Gly  Gly  Trp  Ser  His  Trp  Ser  Pro
    1                       5                   10

( 2 ) INFORMATION FOR SEQ ID NO: 6:

( i ) SEQUENCE CHARACTERISTICS:
        ( A ) LENGTH:11 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 6:

Gly  Gly  Trp  Ser  His  Trp  Ser  Pro  Trp  Ser  Ser
    1                   5                   10

( 2 ) INFORMATION FOR SEQ ID NO: 7:

( i ) SEQUENCE CHARACTERISTICS:
        ( A ) LENGTH:17 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 7:

Lys  Arg  Phe  Lys  Gln  Asp  Gly  Gly  Trp  Ser  His  Trp  Ser  Pro
    1                   5                   10

```
            Trp  Ser  Ser
            15
```

( 2 ) INFORMATION FOR SEQ ID NO: 8:

( i ) SEQUENCE CHARACTERISTICS:
        ( A ) LENGTH:8 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 8:

```
       Ser  His  Trp  Ser  Pro  Trp  Ser  Ser
       1                  5
```

( 2 ) INFORMATION FOR SEQ ID NO: 9:

( i ) SEQUENCE CHARACTERISTICS:
        ( A ) LENGTH:6 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 9:

```
       Gly  Gly  Trp  Ser  Lys  Trp
       1                  5
```

( 2 ) INFORMATION FOR SEQ ID NO: 10:

( i ) SEQUENCE CHARACTERISTICS:
        ( A ) LENGTH:6 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 10:

```
       Gly  Gly  Tyr  Ser  His  Trp
       1                  5
```

( 2 ) INFORMATION FOR SEQ ID NO: 11:

( i ) SEQUENCE CHARACTERISTICS:
        ( A ) LENGTH:6 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 11:

```
       Gly  Gly  Trp  Ser  His  Tyr
       1                  5
```

( 2 ) INFORMATION FOR SEQ ID NO: 12:

( i ) SEQUENCE CHARACTERISTICS:
        ( A ) LENGTH:6 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 12:

```
       Gly  Gly  Trp  Thr  His  Trp
       1                  5
```

( 2 ) INFORMATION FOR SEQ ID NO: 13:

( i ) SEQUENCE CHARACTERISTICS:
    ( A ) LENGTH:6 amino acids
    ( B ) TYPE:amino acids
    ( D ) TOPOLOGY:linear ( i i ) MOLECULE TYPE:peptide ( x i ) SEQUENCE DESCRIPTION:SEQ ID NO: 13:

Gly Gly Trp Ala His Trp
    1                   5

( 2 ) INFORMATION FOR SEQ ID NO: 14:

( i ) SEQUENCE CHARACTERISTICS:
        ( A ) LENGTH: 5 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 14:

Gly Trp Ser His Trp
        1                5

( 2 ) INFORMATION FOR SEQ ID NO: 15:

( i ) SEQUENCE CHARACTERISTICS:
        ( A ) LENGTH:6 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 15:

Asp Gly Trp Ser His Trp
        1                   5

( 2 ) INFORMATION FOR SEQ ID NO: 16:

( i ) SEQUENCE CHARACTERISTICS:
        ( A ) LENGTH:5 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 16:

Gly Arg Gly Asp Ser
        1                5

( 2 ) INFORMATION FOR SEQ ID NO: 17:

( i ) SEQUENCE CHARACTERISTICS:
        ( A ) LENGTH:10 amino acids
        ( B ) TYPE:amino acids
        ( D ) TOPOLOGY:linear ( i i ) MOLECULE TYPE:peptide ( x i ) SEQUENCE DESCRIPTION:SEQ ID NO: 17:

Gly Trp Ser His Ala Ser Pro Trp Ser Ser
        1               5                  10

( 2 ) INFORMATION FOR SEQ ID NO: 18:

( i ) SEQUENCE CHARACTERISTICS:
        ( A ) LENGTH:6 amino acids
        ( B ) TYPE:amino acids
        ( D ) TOPOLOGY:linear (i i) MOLECULE TYPE:peptide (x i) SEQUENCE DESCRIPTION:SEQ ID NO: 18:

```
        Gly   Gly   Trp   Phe   His   Trp
        1                       5
```

(2) INFORMATION FOR SEQ ID NO: 19:

(i) SEQUENCE CHARACTERISTICS:
        (A) LENGTH: 5 amino acids
        (B) TYPE:amino acids
        (D) TOPOLOGY:linear (i i) MOLECULE TYPE:peptide (x i) SEQUENCE DESCRIPTION:SEQ ID NO: 19:

```
        Gly   Trp   Lys   His   Trp
        1                       5
```

(2) INFORMATION FOR SEQ ID NO: 20:

(i) SEQUENCE CHARACTERISTICS:
        (A) LENGTH:6 amino acids
        (B) TYPE:amino acids
        (D) TOPOLOGY:linear (i i) MOLECULE TYPE:peptide (x i) SEQUENCE DESCRIPTION:SEQ ID NO: 20:

```
        Gly   Gly   Trp   Gly   Pro   Trp
        1                       5
```

(2) INFORMATION FOR SEQ ID NO: 21:

(i) SEQUENCE CHARACTERISTICS:
        (A) LENGTH:6 amino acids
        (B) TYPE:amino acids
        (D) TOPOLOGY:linear (i i) MOLECULE TYPE:peptide (x i) SEQUENCE DESCRIPTION:SEQ ID NO: 21:

```
        Ala   Ala   Trp   Ser   His   Trp
        1                       5
```

(2) INFORMATION FOR SEQ ID NO: 22:

(i) SEQUENCE CHARACTERISTICS:
        (A) LENGTH:6 amino acids
        (B) TYPE:amino acids
        (D) TOPOLOGY:linear (i i) MOLECULE TYPE:peptide (x i) SEQUENCE DESCRIPTION:SEQ ID NO: 22:

```
        Asp   Gly   Trp   Ser   His   Trp
        1                       5
```

(2) INFORMATION FOR SEQ ID NO: 23:

(i) SEQUENCE CHARACTERISTICS:
        (A) LENGTH:6 amino acids
        (B) TYPE:amino acids
        (D) TOPOLOGY:linear (i i) MOLECULE TYPE:peptide (x i) SEQUENCE DESCRIPTION:SEQ ID NO: 23:

```
         Trp Ser His Trp Ser Pro
         1               5
```

(2) INFORMATION FOR SEQ ID NO: 24:

(i) SEQUENCE CHARACTERISTICS:
        (A) LENGTH:6 amino acids
        (B) TYPE:amino acids
        (D) TOPOLOGY:linear (i i) MOLECULE TYPE:peptide (x i) SEQUENCE DESCRIPTION:SEQ ID NO: 24:

```
         Gly Gly Trp Thr His Trp
         1               5
```

(2) INFORMATION FOR SEQ ID NO: 25:

(i) SEQUENCE CHARACTERISTICS:
        (A) LENGTH:5 amino acids
        (B) TYPE:amino acids
        (D) TOPOLOGY:linear (i i) MOLECULE TYPE:peptide (x i) SEQUENCE DESCRIPTION:SEQ ID NO: 25:

```
         Gly Arg Gly Ala Ser
         1               5
```

(2) INFORMATION FOR SEQ ID NO: 26:

(i) SEQUENCE CHARACTERISTICS:
        (A) LENGTH:14 amino acids
        (B) TYPE:amino acids
        (D) TOPOLOGY:linear (i i) MOLECULE TYPE:peptide (x i) SEQUENCE DESCRIPTION:SEQ ID NO: 26:

```
         Lys Arg Phe Lys Gln Asp Gly Gly Ala Ser His Ala Ser Phe
         1               5                   10
```

(2) INFORMATION FOR SEQ ID NO: 27:

(i) SEQUENCE CHARACTERISTICS:
        (A) LENGTH:6 amino acids
        (B) TYPE:amino acids
        (D) TOPOLOGY:linear (i i) MOLECULE TYPE:peptide (x i) SEQUENCE DESCRIPTION:SEQ ID NO: 27:

```
         Gln Asp Gly Gly Trp Ser
         1               5
```

(2) INFORMATION FOR SEQ ID NO: 28:

(i) SEQUENCE CHARACTERISTICS:
        (A) LENGTH:6 amino acids
        (B) TYPE:amino acids
        (D) TOPOLOGY:linear (i i) MOLECULE TYPE:peptide (x i) SEQUENCE DESCRIPTION:SEQ ID NO: 28:

```
         Gly Thr Trp Ser Glu Trp
         1               5
```

(2) INFORMATION FOR SEQ ID NO: 29:

(  i  ) SEQUENCE CHARACTERISTICS:
    ( A ) LENGTH:6 amino acids
    ( B ) TYPE:amino acids
    ( D ) TOPOLOGY:linear (  i i  ) MOLECULE TYPE:peptide (  x i  ) SEQUENCE DESCRIPTION:SEQ ID NO: 29:

```
Gly  Phe  Trp  Ser  Glu  Trp
  1              5
```

( 2 ) INFORMATION FOR SEQ ID NO: 30:

(  i  ) SEQUENCE CHARACTERISTICS:
    ( A ) LENGTH:7 amino acids
    ( B ) TYPE:amino acids
    ( D ) TOPOLOGY:linear (  i i  ) MOLECULE TYPE:peptide (  x i  ) SEQUENCE DESCRIPTION:SEQ ID NO: 30:

```
Gly  Gly  Trp  Ser  Lys  Ser  Trp
  1              5
```